United States Patent [19]

Bauer et al.

[11] Patent Number: 5,488,027
[45] Date of Patent: Jan. 30, 1996

[54] HERBICIDE-SAFENER COMBINATIONS CONTAINING SULFONYLUREA OR IMIDAZOLINONE HERBICIDES

[75] Inventors: Klaus Bauer, Hanau; Hermann Bieringer, Eppstein/Taunus, both of Germany

[73] Assignee: Hoechst Aktiengesellschaft, Germany

[21] Appl. No.: 810,211

[22] Filed: Dec. 19, 1991

[30] Foreign Application Priority Data

Dec. 21, 1990 [DE] Germany .................. 40 41 120.6

[51] Int. Cl.⁶ ............................ A01N 25/32; A01N 43/42
[52] U.S. Cl. .............................................. 504/105; 504/104
[58] Field of Search ........................... 504/105, 104

[56] References Cited

U.S. PATENT DOCUMENTS

| | | | |
|---|---|---|---|
| 4,639,266 | 1/1987 | Heubach et al. | 71/92 |
| 4,851,031 | 7/1989 | Bellucci et al. | 71/92 |
| 4,881,966 | 11/1989 | Nyffeler et al. | 71/94 |
| 4,891,057 | 1/1990 | Sohn et al. | 71/72 |
| 4,902,340 | 2/1990 | Hubele | 71/94 |
| 4,944,790 | 7/1990 | Moser et al. | 71/92 |

FOREIGN PATENT DOCUMENTS

| | | |
|---|---|---|
| 89/34951 | 11/1989 | Australia . |
| 1240531 | 8/1987 | Canada . |
| 0094349 | 11/1983 | European Pat. Off. . |
| 0147365 | 7/1985 | European Pat. Off. . |
| 0159287 | 10/1985 | European Pat. Off. . |
| 0191736 | 8/1986 | European Pat. Off. . |
| 0174562 | 1/1987 | European Pat. Off. . |
| 0268554 | 5/1988 | European Pat. Off. . |
| 0269806 | 6/1988 | European Pat. Off. . |
| 0333131 | 9/1989 | European Pat. Off. . |
| 0346620 | 12/1989 | European Pat. Off. . |
| 89/1960 | of 0000 | South Africa . |
| 9110660 | 7/1991 | WIPO . |

OTHER PUBLICATIONS

The Agrochemicals Handbook, Third Ed., Royal Soc. of Chemistry, England, 1991.
J. C. Caseley et al., "Herbicide Resistance in Weeds and Crops", Butterworth–Heinemann Ltd., (1991), pp. 293–303.
Barrett in "Crop Safeners for Herbicides", Academic Press, Inc. (1989), pp. 195–220.
Search Report for EPA 91121623.2.

*Primary Examiner*—Allen J. Robinson
*Assistant Examiner*—B. Bembenick
*Attorney, Agent, or Firm*—Curtis, Morris & Safford

[57] ABSTRACT

The invention relates to herbicidal compositions which contain an effective amount of A) one or more herbicides selected from the group comprising sulfonylureas and imidazolinones and B) one or more safeners selected from the group comprising
  B1) phenyl-substituted imidazole-, imidazoline- and triazolecarboxylic acid derivatives and the benzyloxazolinecarboxylic acid derivatives and/or
  B2) quinolin-8-oxyalkanecarboxylic acid derivatives, with the exception of combinations of imidazolinones with compounds of the formula B2.

The compositions are particularly suitable for protecting plants against phytotoxic secondary effects of sulfonylurea herbicides and imidazolinone herbicides. In the case of the imidazolinone herbicides, the invention also relates to a method of protecting corn plants, by applying post-emergence an effective amount of a quinolin-8-oxyalkanecarboxylic acid derivative together with the imidazolinone herbicide to the plants or the area under cultivation.

11 Claims, No Drawings

HERBICIDE-SAFENER COMBINATIONS CONTAINING SULFONYLUREA OR IMIDAZOLINONE HERBICIDES

The invention relates to the technical field of the crop protection agents, in particular combinations of active substance and antidote which are highly suitable for use against harmful plants in crops of useful plants.

Some of the more recent herbicidal active substances are highly active and highly selective and can be used against a broad range of various broad-leaved weeds and/or grass weeds and specific stands of crop plants such as soya beans or corn or cereals. However, other crop plants are damaged by these herbicides so that they cannot be used in such crops at all or only at application rates which do not guarantee the optimum broad herbicidal activity.

Examples of such herbicides whose use is only limited are some herbicides from amongst the group selected of the sulfonylureas and imidazolinones. Herbicides of these two structural groups are related in as far as they block partly the same pathways of biosynthesis in the plant metabolism. Both herbicide classes inhibit primarily the enzyme acetolactate synthase, also termed acetohydroxyacid synthase (AHAS), an important key enzyme which plays an important role in the biosynthesis of the branched-chain amino acids valine, leucine and isoleucine (see, for example, Dale L. Shaner et al.: Imidazolinones, Potent Inhibitors of Acetohydroxyacid Synthase, Plant. Physiol. 76 (1984) 545–546; E. M. Beyer et al. "Sulfonylurea Herbicides" in "Herbicides: Chemistry, Degradation and Mode of Action" Vol. 3, M. Dekker, Inc., Ed. by P. G. Kearney and D. D. Kaufmann, New York, 1987).

Even though imidazolinones and sulfonylureas differ greatly with regard to other properties such as, inter alia, application rate and soil activity, so that equivalence is not the case, the herbicides from these substance classes can have properties in common because the mechanism of action in the plant metabolism is partly identical. For example, many herbicides of the substance classes mentioned cannot be used selectively in cereal crops and/or not in corn because these crop plants are damaged, at least at the dosage rates desired, which are required for a broad herbicidal activity against broad-leaved weeds and grass weeds.

It would be desirable to protect the crop plants mentioned against the damaging effect of the herbicides mentioned with the aid of a safener (or antidote) without considerably reducing the effect of the herbicides mentioned against the harmful plants.

There is already known a large number of safeners which are very different as regards their structure and which are employed in combination with herbicides. However, they are mostly unsuitable for a combination with sulfonylureas or imidazolinones in cereal crops (for example wheat, barley) or corn.

EP-A-94,349 discloses safeners from the quinolin-8-oxyalkanecarboxylic acid series, which are mainly recommended for use with aryloxy- and heteroaryloxy-phenoxycarboxylic acid herbicides. The publication mentions sulfonylureas amongst the large number of structurally different herbicides as possible herbicides for a combination with the safeners; there are also mentioned two examples in which wheat seed is dressed with a methyl quinolinoxyacetate and the area under cultivation is treated with a sulfonylurea post-emergence or pre-emergence. However, the safener action of the known sulfonylurea/safener combination is not sufficient, in particular not for the use of safener and herbicide post-emergence in cereals, such as wheat or barley, or in corn.

U.S. Pat. No. 4,851,031 discloses the imidazolinone herbicides such as imazaquin, imazapyr or imazethapyr can be used with safeners from the quinolin-8-oxyalkanecarboxylic acid series for controlling weeds in cereals, namely preferably by the seed-dressing method, but also by foliar application (post-emergency application) of safener and herbicide together. In a concrete example, other crop plants such as corn are only protected by the seed-dressing technique.

It is known from M. Barrett's paper in "Crop Safeners for Herbicides" by K. K. Hatzios and R. E. Hoagland (Editors) Academic Press, San Diego, Calif. U.S.A. 1989, Chapter 9, p. 209–220 and from K. K. Hatzios' paper in "Herbicides Resistance in Weeds and Crops" (Editors: J. C. Caseley, G. W. Cussans, R. K. Atkin) Butterworth-Heinemann, Oxford, GB 1991, p. 293–303, that the protective action of safeners against herbicide damage caused by imidazolinones is better when the herbicides are employed post-emergence, but the safeners at an earlier point in time as seed-dressing agents or while the crop is seeded (pre-emergence). Safener effects achieved by the method of seed-dressing are therefore not expected to provide a similarly effective or better safener action when the safener is used post-emergence together with the herbicide.

Experiments have now shown totally unexpectedly that crop plants, for example wheat and barley as well as corn, can be protected against undesirable damage of the above-mentioned herbicides when they are applied together with certain compounds which act as herbicidal antidotes or safeners.

It has furthermore been found that imidazolinones and certain safeners of the quinolin-8-oxy series are particularly suitable for the selective post-emergence control of harmful plants in corn crops.

The invention therefore relates to herbicidal compositions which are composed of an effective amount of A) one or more herbicides from the group of the sulfonylureas and imidazolinones and B) one or more compounds of the formulae B1 and B2,

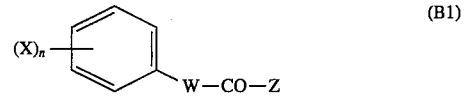

(B1)

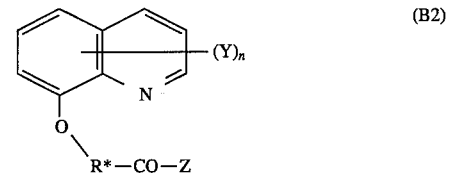

(B2)

in which

X is hydrogen, halogen, $C_1$–$C_4$-alkyl, $C_1$–$C_4$-alkoxy, nitro or $C_1$–$C_4$-haloalkyl, Y is halogen, $C_1$–$C_4$-alkyl, $C_1$–$C_4$-alkoxy, nitro or $C_1$–$C_4$-haloalkyl, R* is a $C_1$–$C_2$-alkylene chain which can additionally be substituted by one or two $C_1$–$C_4$-alkyl radicals, and is preferably —$CH_2$—, Z is $OR^1$, $SR^1$ or $NR^1R$, preferably a radical of the formula $OR^1$, $NHR^1$ or $N(CH_3)$, in particular of the formula $OR^1$, R independently or $R^1$ is hydrogen, $C_1$–$C_6$-alkyl, $C_1$–$C_6$-alkoxy or phenyl or substituted phenyl, or R and $R^1$ together with the nitrogen atom linked to them is a saturated or unsaturated 3- to 7-membered heterocycle which has at least one nitrogen atom and up to 3 hetero atoms and which is unsubstituted or substituted by radicals selected from the group comprising $C_1$–$C_4$-alkyl, $C_1$–$C_4$-alkoxy, phenyl or substituted phenyl, $R^1$ independently of R is hydrogen, $C_1$–$C_{18}$-alkyl, $C_3$–$C_{12}$-cycloalkyl, $C_2$–$C_8$-alkenyl or $C_2$–$C_8$-alkynyl, each of the above carbon-containing radicals independently of one another being unsubstituted or monosubstituted or polysubstituted by radicals selected from the group comprising halogen, hydroxyl, $C_1$–$C_8$-alkoxy, $C_1$–$C_8$-alkylthio, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy, cyano, mono- and di-($C_1$–$C_4$-alkyl)amino, ($C_1$–$C_8$-alkoxy)carbonyl, ($C_2$–$C_8$-alkenyloxy)carbonyl, ($C_1$–$C_8$-alkylthio)carbonyl, ($C_2$–$C_8$-alkynyloxy)carbonyl, ($C_1$–$C_8$-alkyl)carbonyl, ($C_2$–$C_8$-alkenyl)carbonyl, ($C_2$–$C_8$-alkynyl)carbonyl, 1-(hydroxyimino)-$C_1$–$C_6$-alkyl, 1-($C_1$–$C_4$-alkylimino)-$C_1$–$C_6$-alkyl, 1-($C_1$–$C_4$-alkoxyimino)-$C_1$–$C_6$-alkyl, ($C_1$–$C_8$-alkyl)carbonylamino, ($C_2$–$C_8$-alkenyl)carbonylamino, ($C_2$–$C_8$-alkynyl)carbonylamino, aminocarbonyl, ($C_1$–$C_8$-alkyl)aminocarbonyl, di-($C_1$–$C_6$-alkyl)aminocarbonyl, ($C_2$–$C_6$-alkenyl)aminocarbonyl, ($C_2$–$C_6$-alkynyl)aminocarbonyl, ($C_1$–$C_8$-alkoxy)carbonylamino, ($C_1$–$C_8$-alkyl)aminocarbonylamino, $C_1$–$C_6$-alkylcarbonyloxy which is unsubstituted or substituted by halogen, $NO_2$, $C_1$–$C_4$-alkoxy or optionally substituted phenyl, ($C_2$–$C_6$-alkenyl)carbonyloxy, ($C_2$–$C_6$-alkynyl)carbonyloxy, $C_1$–$C_8$-alkylsulfonyl, phenyl, phenyl-$C_1$–$C_6$-alkoxy, phenyl-($C_1$–$C_6$-alkoxy)carbonyl, phenoxy, phenoxy-$C_1$–$C_6$-alkoxy, phenoxy-($C_1$–$C_6$-alkoxy)carbonyl, phenylcarbonyloxy, phenylcarbonylamino, phenyl-($C_1$–$C_6$-alkyl)carbonylamino, where the 9 last-mentioned radicals in the phenyl ring are unsubstituted or monosubstituted or polysubstituted by radicals from the group comprising halogen, $C_1$–$C_4$-alkyl, $C_1$–$C_4$-alkoxy, $C_1$–$C_4$-haloalkyl, $C_1$–$C_4$-haloalkoxy and nitro, and radicals of the formulae —$SiR'_3$, —O—$SiR'_3$, $(R')_3Si$—$C_1$–$C_6$-alkoxy, —CO—O—$NR'_2$, —O—N=$CR'_2$, —N=$CR'_2$, —O—$NR'_2$—$CH(OR')_2$ and —O—$(CH_2)_m$—$CH(OR')_2$, where the R' radicals in the formulae mentioned independently of each other are hydrogen, $C_1$–$C_4$-alkyl or phenyl which is unsubstituted or monosubstituted or polysubstituted by radicals selected from the group comprising halogen, $C_1$–$C_4$-alkyl, $C_1$–$C_4$-alkoxy, $C_1$–$C_4$-haloalkyl, $C_1$–$C_4$-haloalkoxy and nitro, or, in pairs, are an $C_2$–$C_6$-alkylene chain and m=0 to 6, and an alkoxy radical of the formula R"O—CHR'"(OR")-$C_1$–$C_6$-alkoxy where the R" radicals independently of each other are $C_1$–$C_4$-alkyl or together are a $C_1$–$C_6$-alkylene group, and R'" is hydrogen or $C_1$–$C_4$-alkyl, n is an integer from 1 to 5, preferably 1 to 3, and W is a divalent heterocyclic radical having 5 ring atoms of the formulae W1 to W4,

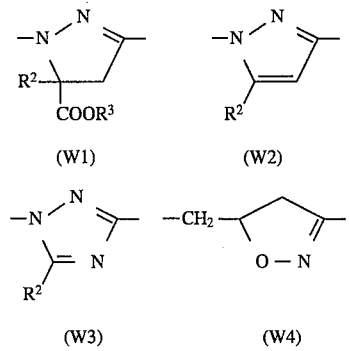

in which $R^2$ is hydrogen, $C_1$–$C_8$-alkyl, $C_1$–$C_8$-haloalkyl, $C_3$–$C_{12}$-cycloalkyl or optionally substituted phenyl, and $R^3$ is hydrogen, $C_1$–$C_8$-alkyl, $C_1$–$C_8$-haloalkyl, ($C_1$–$C_4$-alkoxy)-$C_1$–$C_4$-alkyl, $C_1$–$C_6$-hydroxyalkyl, $C_3$–$C_{12}$-cycloalkyl or tri-($C_1$–$C_4$-alkyl)silyl, with the exception of combinations of imidazolinones with compounds of the formula B2.

Herbicidal compositions according to the invention which are of particular interest are those in which, in the compounds of the formulae B1 and B2, $R^1$ is hydrogen, $C_1$–$C_{12}$-alkyl, $C_3$–$C_7$-cycloalkyl, $C_2$–$C_8$-alkenyl or $C_2$–$C_8$-alkynyl, where each of the above carbon-containing radicals independently of each other is unsubstituted or monosubstituted or polysubstituted by halogen or monosubstituted or disubstituted, preferably up to monosubstituted, by radicals selected from the group comprising hydroxyl, $C_1$–$C_4$-alkoxy, $C_1$–$C_4$-alkylthio, $C_2$–$C_4$-alkenyloxy, $C_2$–$C_4$-alkynyloxy, mono- and di-($C_1$–$C_2$-alkyl)amino, ($C_1$–$C_4$-alkoxy)carbonyl, ($C_2$–$C_4$-alkenyloxy)carbonyl, ($C_2$–$C_4$-alkynyloxy)carbonyl, ($C_1$–$C_4$-alkyl)carbonyl, ($C_2$–$C_4$-alkenyl)carbonyl, ($C_2$–$C_4$-alkynyl)carbonyl, 1-(hydroxyimino)-$C_1$–$C_4$-alkyl, 1-($C_1$–$C_4$-alkylimino)-$C_1$–$C_4$-alkyl, 1-($C_1$–$C_4$-alkoxyimino)-$C_1$–$C_4$-alkyl, $C_1$–$C_4$-alkylsulfonyl, phenyl, phenyl-$C_1$–$C_4$-alkoxy, phenyl-($C_1$–$C_4$-alkoxy)carbonyl, phenoxy, phenoxy-$C_1$–$C_4$-alkoxy, phenoxy-($C_1$–$C_4$-alkoxy) carbonyl, where the 6 last-mentioned radicals are unsubstituted or monosubstituted or polysubstituted in the phenyl ring by radicals selected from the group comprising halogen, $C_1$–$C_2$-alkyl, $C_1$–$C_2$-alkoxy, $C_1$–$C_2$-haloalkyl, $C_1$–$C_2$-haloalkoxy and nitro, and radicals of the formulae —$SiR'_3$, —O—N=$CR'_2$, —N=$CR'_2$ and —O—$NR'_2$, where the R' radicals in the formulae mentioned independently of each other are hydrogen, $C_1$–$C_2$-alkyl or phenyl which is unsubstituted or monosubstituted or polysubstituted by radicals selected from the group comprising halogen, $C_1$–$C_2$-alkyl, $C_1$–$C_2$-alkoxy, $C_1$–$C_2$-haloalkyl, $C_1$–$C_2$-haloalkoxy and nitro, or, in pairs, are a $C_4$–$C_5$-alkylene chain.

Other herbicidal compositions according to the invention which are of particular interest are those in which, in the compounds of the formulae B1 and B2, X is hydrogen, halogen, methyl, ethyl, methoxy, ethoxy or $C_1$–$C_2$-haloalkyl, preferably hydrogen, halogen or $C_1$–$C_2$-haloalkyl, and Y is halogen, methyl, ethyl, methoxy, ethoxy or $C_1$–$C_2$-haloalkyl, preferably hydrogen, halogen or $C_1$–$C_2$-haloalkyl.

Preferred herbicidal compositions according to the invention are those where, in the compounds of the formula B1, X is hydrogen, halogen, nitro or $C_1$-$C_4$-haloalkyl, n is a number from 1 to 3, Z is a radical of the formula $OR^1$, $R^1$ is hydrogen, $C_1$-$C_8$-alkyl or $C_3$-$C_7$-cycloalkyl, where each of the above carbon-containing radicals independently of each other is unsubstituted or monosubstituted or polysubstituted by radicals selected from the group comprising halogen or monosubstituted or disubstituted, preferably unsubstituted or monosubstituted, by radicals selected from the group comprising hydroxyl, $C_1$-$C_4$-alkoxy, ($C_1$-$C_4$-alkoxy)carbonyl, $C_2$-$C_6$-alkenyloxycarbonyl, ($C_2$-$C_6$-alkynyloxy)carbonyl, 1-(hydroxyimino)-$C_1$-$C_4$-alkyl, 1-($C_1$-$C_4$-alkylimino)-$C_1$-$C_4$-alkyl, 1-($C_1$-$C_4$-alkoxyimino)-$C_1$-$C_4$-alkyl, and radicals of the formulae —$SiR'_3$, —O—N=$CR'_2$, —N=$CR'_2$ and —O—$NR'_2$, in which the R' radicals in the formulae mentioned independently of each other are hydrogen or $C_1$-$C_4$-alkyl or, in pairs, are a $C_4$-$C_5$-alkylene chain, $R^2$ is hydrogen, $C_1$-$C_8$-alkyl, $C_1$-$C_6$-haloalkyl, $C_3$-$C_7$-cycloalkyl or phenyl and $R^3$ is hydrogen, $C_1$-$C_8$-alkyl, $C_1$-$C_8$-haloalkyl, ($C_1$-$C_4$-alkoxy)-$C_1$-$C_4$-alkyl, $C_1$-$C_6$-hydroxyalkyl, $C_3$-$C_7$-cycloalkyl or tri-($C_1$-$C_4$-alkyl)silyl.

Other preferred herbicidal compositions according to the invention are those in which, in the compounds of the formula B2, Y is halogen or $C_1$-$C_4$-haloalkyl and n is a figure from 1 to 3, preferably $(Y)_n$=5-Cl, Z is a radical of the formula $OR^1$, R* is $CH_2$ and $R^1$ is hydrogen, $C_1$-$C_8$-alkyl, $C_1$-$C_8$-haloalkyl or ($C_1$-$C_4$-alkoxy)-$C_1$-$C_4$-alkyl, 1-(hydroxyimino)-$C_1$-$C_4$-alkyl, 1-($C_1$-$C_4$-alkylimino)-$C_1$-$C_3$-alkyl, 1-($C_1$-$C_2$-alkoxyimino)-$C_1$-$C_3$-alkyl, preferably $C_1$-$C_8$-alkyl.

Particularly preferred herbicidal compositions according to the invention are those with compounds of the formula B1 in which W is W1, X is H, halogen or $C_1$-$C_2$-haloalkyl and n=1–3, in particular $(X)_n$= 2,4-$Cl_2$, Z is a radical of the formula $OR^1$, $R^1$ is hydrogen, $C_1$-$C_8$-alkyl, $C_1$-$C_4$-haloalkyl, $C_1$-$C_4$-hydroxyalkyl, $C_3$-$C_7$-cycloalkyl, ($C_1$-$C_4$-alkoxy)-$C_1$-$C_4$-alkyl, tri-($C_1$-$C_2$-alkyl)silyl, preferably $C_1$-$C_4$-alkyl, $R^2$ is hydrogen, $C_1$-$C_8$-alkyl, $C_1$-$C_4$-haloalkyl or $C_3$-$C_7$-cycloalkyl, preferably hydrogen or $C_1$-$C_4$-alkyl, and $R^3$ is hydrogen, $C_1$-$C_8$-alkyl, $C_1$-$C_4$-haloalkyl, $C_1$-$C_4$-hydroxyalkyl, $C_3$-$C_7$-cycloalkyl, ($C_1$-$C_4$-alkoxy)-$C_1$-$C_4$-alkyl or tri-($C_1$-$C_2$-alkyl) silyl, preferably H or $C_1$-$C_4$-alkyl.

Other particularly preferred herbicidal compositions according to the invention are those with compounds of the formula B1 in which W is W2, X is H, halogen or $C_1$-$C_2$-haloalkyl and n=1–3, in particular $(X)_n$=2,4-$Cl_2$, Z is a radical of the formula $OR^1$, $R^1$ is hydrogen, $C_1$-$C_8$-alkyl, $C_1$-$C_4$-haloalkyl, $C_1$-$C_4$-hydroxyalkyl, $C_3$-$C_7$-cycloalkyl, ($C_1$-$C_4$-alkoxy)-$C_1$-$C_4$-alkyl, tri-($C_1$-$C_2$-alkyl)silyl, preferably $C_1$-$C_4$-alkyl and $R^2$ is hydrogen, $C_1$-$C_8$-alkyl, $C_1$-$C_4$-haloalkyl, $C_3$-$C_7$-cycloalkyl or phenyl, preferably hydrogen or $C_1$-$C_4$-alkyl.

Other particularly preferred herbicidal compositions according to the invention are those with compounds of the formula B1 in which W is W3, X is H, halogen or $C_1$-$C_2$-haloalkyl and n=1–3, in particular $(X)_n$=2,4-$Cl_2$, Z is a radical of the formula $OR^1$, $R^1$ is hydrogen, $C_1$-$C_8$-alkyl, $C_1$-$C_4$-haloalkyl, $C_1$-$C_4$-hydroxyalkyl, $C_3$-$C_7$-cycloalkyl, ($C_1$-$C_4$-alkoxy)-$C_1$-$C_4$-alkyl, tri-($C_1$-$C_2$-alkyl) silyl, preferably $C_1$-$C_4$-alkyl and $R^2$ is $C_1$-$C_8$-alkyl or $C_1$-$C_4$-haloalkyl, preferably $C_1$-haloalkyl.

Other particularly preferred herbicidal compositions according to the invention are those with compounds of the formula B1 in which W is W4, X is hydrogen, halogen, nitro, $C_1$-$C_4$-alkyl, $C_1$-$C_2$-haloalkyl, preferably $CF_3$, or $C_1$-$C_4$-alkoxy, n is 1 to 3, Z is a radical of the formula $OR^1$, $R^1$ is hydrogen, $C_1$-$C_4$-alkyl, or ($C_1$-$C_4$-alkoxy)carbonyl-$C_1$-$C_4$-alkyl, preferably a radical of the formula ($C_1$-$C_4$-alkoxy)—CO—$CH_2$—, ($C_1$-$C_4$-alkoxy)—CO—C($CH_3$)H—, HO—CO—$CH_2$ or HO—CO—C($CH_3$)H.

In the formulae, alkyl, alkenyl and alkynyl are straight-chain or branched; the same applies to substituted alkyl, ankenyl and alkynyl radicals such as haloalkyl, hydroxyalkyl, alkoxycarbonyl etc.; alkyl is, for example, methyl, ethyl, n- and i-propyl, n-, i-, t- and 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl is, for example, allyl, 1-methylprop-2-en-1-yl, but-2-en-1-yl, but-3-en-1-yl, 1-methylbut-3-ene and 1-methylbut-2-ene; alkynyl is, for example, propargyl, but-2-in-1-yl, but-3-in-1-yl, 1-methylbut-3-in; halogen is fluorine, chlorine, bromine or iodine, preferably fluorine, chlorine or bromine, particularly fluorine or chlorine; haloalkyl, -alkenyl and -alkynyl are halogen-substituted alkyl, alkenyl or alkynyl, for example $CF_3$, $CHF_2$, $CH_2F$, $CF_3CF_2$, $CH_2FCHCl$ $CCl_3$, $CHCl_2$, $CH_2CH_2Cl$; haloalkoxy is, for example, $OCF_3$, $OCHF_2$, $OCH_2F$, $CF_3CF_2O$, $CF_3CH_2O$; optionally substituted phenyl is phenyl or substituted phenyl; substituted phenyl is phenyl which is mono-substituted or polysubstituted by radicals selected from the group comprising halogen, $C_{-C4}$-alkyl, $C_1$-$C_4$-alkoxy, $C_1$-$C_4$-haloalkyl, $C_1$-$C_4$-haloalkoxy and nitro, for example o-, m- and p-tolyl, dimethylphenyls, 2-, 3- and 4-chlorophenyl, 2-, 3- and 4-trifluoro- and- trichlorophenyl, 2,4-, 3,5-, 2,5- and 2,3-dichlorophenyl, and o-, m- and p-methoxyphenyl.

The compounds of the formula B1 are known from EP-A-0,333,131 (ZA-89/1960), EP-A-0,269,806 (U.S. Pat. No. 4,891,057), EP-A-0,346,620 (AU-A-89/34951) , WO-91/08202 (International Patent Application PCT/EP 90/01,966 ) and WO 91/07874 (International Patent Application No. PCT/EP 90/02020) and literature cited therein, or they can be prepared by the, or in analogy with, the processes described therein. The compounds of the formula B2 are known from EP-A-94,349 (U.S. Pat. No. 4,902,340)

, EP-A-0,191,736 (U.S. Pat. No. 4,881,966) and from German Patent Application P 4041121.4 and the literature cited therein, or they can be prepared by, or in analogy with, the process as described therein.

Suitable herbicides of the A type are, according to the invention, sulfonylurea derivatives which, on their own, cannot be employed, or not optimally employed, in cereal crops and/or corn because they inflict too severe damage on the crop plants. Examples of such sulfonylureas are 1) Phenylsulfonylureas, for example
   a) chlorimuron ethyl (see Agricultural Chemicals Book II "Herbicides" by W. T. Thompson, Thompson Publications, Fresno Calif., U.S.A. 1990, page 152); presently used in soya beans, but not in cereals or corn;
   b) primisulfuron (CGA 136,872, see Brighton Crop Prot. Conf.—Weeds—1989, p. 41–48),
   c) 3-(4-ethyl-6-methoxy-1,3,5-triazin-2-yl)-1-(2,3-dihydro-1,1-dioxo-2 -methylbenzo[b]thiophen-7-sulfonyl)-urea (see EP-A-79,683),
   d) 3-(4-ethoxy-6-ethyl-1,3,5-triazin-2-yl)-1-(2,3-dihydro-1,1-dioxo-2 -methylbenzo[b]thiophen-7-sulfonyl)urea (see EP-A-79,683),
   e) tribenuron-methyl (see "The Pesticide Manual", British Crop Protection Council 9th Edition (1990/91), page 840),
   f) metsulfuron-methyl (see Proc. Int. Congr. Plant Prot., 10th, 1983, Vol. 1, 324),
   g) chlorsulfuron (see U.S. Pat. No. 4,127,405; Weeds Weed Control, 1980, 21st, 24),
   h) triasulfuron (see "The Pesticide Manual" 9th Ed., p. 837) and
   i) sulfometuron-methyl (see "The Pesticide Manual" 9th Ed., p. 774);

2) Thienylsulfonylureas, for example thifensulfuron-methyl (see Agricultural Chemicals Book II "Herbicides" by W. T. Thompson, Thompson Publications, Fresno Calif., U.S.A. 1990, page 155);

3) Pyrazolylsulfonylureas, for example
   a) pyrazosulfuron-ethyl (NC 311, see "The Pesticide Manual" 9th Ed., p. 735) and
   b) methyl 3-chloro-5-(4,6-dimethoxypyrimidin-2-yl-carbamoylsulfamoyl)-1-methyl-pyrazole-4-carboxylate (see EP 282,613);

4) Sulfonediamide derivatives, for example amidosulfuron and structural analogs (see EP-A-0,131,258 and Z. Pfl.Krankh. Pfl.Schutz, Special Issue XII, 489–497 (1990); presently not used in corn;

5) Pyridylsulfonylureas, for example
   a) nicosulfuron (SL-950, see Kimura et al., Brighton Crop Protection Conference—Weeds— 1989, p. 29–34); not used in cereals on its own;
   b) DPX-E 9636 (see Brighton Crop Prot. Conf.—Weeds—1989, p. 23 et seq.); presently not used in cereals;
   c) Pyridylsulfonylureas as are described in German Patent Applications P 4000503.8 (WO-91/10660) and P 4030577.5, preferably those of the formula A1 or their salts,

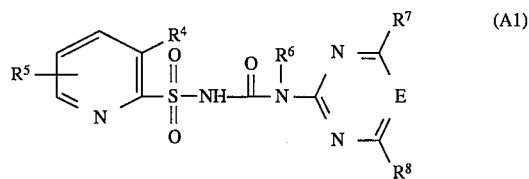

in which
E is CH or N, preferably CH,
$R^4$ is iodine or $NR^9R^{10}$,
$R^5$ is H, halogen, cyano, $C_1$–$C_3$-alkyl, $C_1$–$C_3$-alkoxy, $C_1$–$C_3$-haloalkyl, $C_1$–$C_3$-haloalkoxy, $C_1$–$C_3$-alkylthio, ($C_1$–$C_3$-alkoxy)-$C_1$–$C_3$-alkyl, ($C_1$–$C_3$-alkoxy)carbonyl, mono- or di-($C_1$–$C_3$-alkyl)-amino, $C_1$–$C_3$-alkylsulfinyl or -sulfonyl, $SO_2$-$NR^aR^b$ or $CO$-$NR^aR^b$, particularly H,
$R^a$ and $R^b$ independently of each other are H, $C_1$–$C_3$-alkyl, $C_1$–$C_3$-alkenyl, $C_1$–$C_3$-alkynyl or together are —$(CH_2)_4$—, —$(CH_2)_5$— or —$(CH_2)_2$—O—$(CH_2)_2$—,
$R^6$ is H or $CH_3$
$R^7$ is halogen, $C_1$–$C_2$-alkyl, $C_1$–$C_2$-alkoxy, $C_1$–$C_2$-haloalkyl, preferably $CF_3$, $C_1$–$C_2$-haloalkoxy, preferably $OCHF_2$ or $OCH_2CF_3$,
$R^8$ is $C_1$–$C_2$-alkyl, $C_1$–$C_2$-haloalkoxy, preferably $OCHF_3$ or $C_1$–$C_2$-alkoxy, and
$R^9$ is $C_1$–$C_4$-alkyl and $R^{10}$ is $C_1$–$C_4$-alkylsulfonyl or $R^9$ and $R^{10}$ together are a chain of the formula —$(CH_2)_3SO_2$— or —$(CH_2)_4SO_2$—, 6) Phenoxysulfonylureas such as are known, for example, from EP-A-0,342,569, EP-A-4,163, EP-A-113,956, U.S. Pat. No. 4,678,500 and U.S. Pat. No. 4,581,059, preferably alkoxyphenoxysulfonylureas of the formula A2 or their salts,

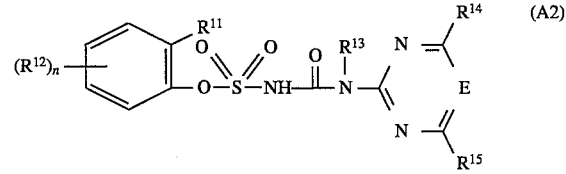

in which
E is CH or N, preferably CH,
$R^{11}$ is ethoxy, propoxy or isopropoxy,
$R^{12}$ is hydrogen, halogen, $NO_2$, $CF_3$, CN, $C_1$–$C_4$-alkyl, $C_1$–$C_4$-alkoxy, $C_1$–$C_4$-alkylthio or ($C_1$–$C_3$-alkoxy)carbonyl, preferably in the 6-position on the phenyl ring.
n is 1, 2 or 3, preferably 1,
$R^{13}$ is hydrogen, $C_1$–$C_4$-alkyl or $C_3$–$C_4$-alkenyl,
$R^{14}$ and $R^{15}$ independently of each other are halogen, $C_1$–$C_2$-alkyl, $C_1$–$C_2$-alkoxy, $C_1$–$C_2$-haloalkyl, $C_1$–$C_2$-haloalkoxy or ($C_1$–$C_2$-alkoxy)-$C_1$–$C_2$-alkyl, preferably $OCH_3$ or $CH_3$,
and other related sulfonylurea derivatives, and mixtures of these.

Other suitable herbicides of the A type are, according to the invention, active substances from the group of the imidazolinone derivatives which are well tolerated in some crops because of their selectivity, for example in soybeans, but cannot be used in cereal and/or corn crops. Examples of such active substances are 11) imazethapyr (see Ch. R. Worthing's "The Pesticide Manual" 8th Edition 1987, by British Crop Protection Council, page 473), 12) imazaquin (see Ch. R. Worthing's "The Pesticide Manual" 8th Edition 1987, by British Crop Protection Council, page 474), 13) imazethamethapyr (chemical name: rac-2-[4,5-dihydro4-methyl-4-(1-methylethyl)-5 -oxo-1H-imidazol-2-yl]-5-methyl-3-pyridine-carboxylic acid; see Weed Techn. 1991 (5), 430–433 and 434–438) and other related compounds and mixtures of these.

Mixtures of various sulfonylurea derivatives and/or various imidazolinones are also suitable according to the invention.

The following groups of compounds have proven suitable as safeners for the abovementioned herbicides:

a) Compounds of the dichlorophenylpyrazoline-3-carboxylic acid type (i.e. of the formula B1 in which $W=W1$ and $(X)_n=2,4$-$Cl_2$), preferably compounds such as (B1-1) ethyl 1-(2,4-dichlorophenyl)-5-(ethoxycarbonyl)-5-methyl-2-pyrazoline-3-carboxylate and related compounds as are described in WO-91-/07874 (International Patent Application No. PCT/EP 90/02020), b) Dichlorophenylpyrazolecarboxylic acid derivatives (i.e. of the formula B1 in which $W=W2$ and $(X)_n=2,4$-$Cl_2$), preferably compounds such as (B1-2) ethyl 1-(2,4-dichlorophenyl)-5-methylpyrazole-3-carboxylate, (B1-3) ethyl 1-(2,4-dichlorophenyl)-5-isopropylpyrazole-3-carboxylate, (B1-4) ethyl 1-(2,4-dichlorophenyl)-5-(1,1-dimethylethyl)-pyrazole-3-carboxylate, (B1-5) ethyl 1-(2,4-dichlorophenyl)-5-phenylpyrazole-3-carboxylate and related compounds as are described in EP-A-0,333,131 and EP-A-0,269,806.

c) Compounds of the triazolecarboxylic acid type (i.e. of the formula B1 in which $W=W3$ and $(X)_n=2,4$-$Cl_2$), preferably compounds such as (B1-6) ethyl 1-(2,4-dichlorophenyl)-5-trichloromethyl-(1H)-1,2,4-triazole-3-carboxylate (fenchlorazol)

and related compounds (see EP-A-0,174,562 and EP-A-0,346,620);

d) Compounds of the dichlorobenzyl-2-isoxazoline-3-carboxylic acid type (i.e. of the formula B1 in which $W=W4$ and $(X)_n=2,4$-$Cl_2$), preferably compounds such as (B1-7) ethyl 5-(2,4-dichlorobenzyl)-2-isoxazoline-3-carboxylate and related compounds as are described in WO-91/08202 (International Patent Application No. PCT/EP 90/01966).

e) Compounds of the dichlorophenylpyrazoline-3-carboxylate type, for example (B1-8) 3-ethyl 5-t-butyl 1-(2,4-dichlorophenyl)pyrazoline-3,5-dicarboxylate, as they are described in WO-91/07874, f) Compounds of the (5-chloro-8-quinolinoxy)acetic acid type (i.e. of the formula B2 in which $(Y)_n=5$-Cl, $Z=OR^1$, $R^*=CH_2$), preferably compounds such as (B2-1) 1-methylhex-1-yl 2-(5-chloro-8-quinolinoxy)acetate, (B2-2) 1,3-dimethylbut-1-yl 2-(5-chloro-8-quinolinoxy)acetate, (B2-3) 4-methylpent-2-yl 2-(5-chloro-8-quinolinoxy)acetate, (B2-4) 2-heptyl 2-(5-chloro-8-quinolinoxy)acetate, (B2-5) 2-allyloxy-1-methylethyl 2-(5-chloro-8-quinolinoxy)acetate, (B2-6) ethyl 2-(5-chloro-8-quinolinoxy)acetate, (B2-7) 2-phenoxyethyl 2-(5-chloro-8-quinolinoxy)acetate, (B2-8) 2-methyl-1-propen-3-yl 2-(5-chloro-8-quinolinoxy)acetate, (B2-9) 2-methyl-3-oxobutyl 2-(5-chloro-8-quinolinoxy)acetate, (B2-10) 2-(pent-3-ylidene-iminooxy)ethyl 2-(5-chloro-8-quinolinoxy)acetate, (B2-11) (2,2-dimethyl-1,3-dioxolan-4-yl)methyl 2-(5-chloro-8-quinolinoxy)acetate, (B2-12) (allyloxycarbonyl)methyl 2-(5-chloro-8-quinolinoxy)acetate, (B2-13) 2-(isopropylidene-iminooxy)ethyl 2-(5-chloro-8-quinolinoxy)acetate, (B2-14) trimethylsilylmethyl 2-(5-chloro-8-quinolinoxy)acetate, (B2-15) 2-(trifluoromethylcarbonylamino)ethyl 2-(5-chloro-8-quinolinoxy)acetate, (B2-16) 2-(methoxyimino)propyl 2-(5-chloro-8-quinolinoxy)acetate, (B2-17) 4-(acetoxyimino)pentyl 2-(5-chloro-8-quinolinoxy)acetate, (B2-18) 2-(benzamido)ethyl 2-(5-chloro-8-quinolinoxy)acetate, (B2-19) 4-(hydroxyimino)pentyl 2-(5-chloro-8-quinolinoxy)acetate, (B2-20) 2-(acetoxy)ethyl 2-(5-chloro-8-quinolinoxy)acetate, (B2-21) 2-(2-methylprop-2-en-1-yl)ethyl 2-(5-chloro-8-quinolinoxy)acetate, (B2-22) 3-(propargyloxy)propyl 2-(5-chloro-8-quinolinoxy)acetate, (B2-23) N,N-dimethyl-2-(5-chloro-8-quinolinoxy)acetamide, (B2-24) N-(2-acetoxyethyl)2-(5-chloro-8-quinolinoxy)acetamide, (B2-25) 2-(allyloxy)propyl 2-(5-chloro-8-quinolinoxy)acetate and related compounds as are described in EP-A-94,349 (U.S. Pat. No. 4,902,340), EP-A-0,191,736 (U.S. Pat. No. 4,881,966) and in German Patent Application P 4041121.4.

The safeners (antidotes) of the above groups a) to f) reduce or prevent phytotoxic effects which can occur when the herbicides A) are employed in crops of useful plants, without impairing the effectiveness of these herbicides against harmful plants. This allows the field of application of conventional crop protection agents to be broadened very substantially and to be extended to, for example, crops such as wheat, barley, corn and other Gramineae crops in which use of the herbicides had previously not been possible, or only to a limited extent, i.e. at low dosage rates with a poor spectrum of action.

The herbicidal active substances and the safeners mentioned can be applied together (as a finished formulation or by the tank mix method) or in succession in any desired sequence. The ratio by weight of safener: herbicide can be varied within wide limits and is preferably in the range from 1:10 to 10:1, in particular 1:10 to 5:1. The amounts of herbicide and safener which are optimal in each case depend on the type of the herbicide used or on the safener used, as well as on the nature of the plant stand to be treated, and can be determined in each individual case by suitable preliminary experiments.

The main fields of application for the use of the safeners are, above all, cereal crops (wheat, rye, barley, oats), rice, corn, sorghum, but also cotton and soybeans, preferably cereals and corn.

The safeners of the B type can be used for pretreating the seed of the crop plant (seed dressing) or incorporated into the seed furrows prior to drilling, or applied together with the herbicide before or after emergence of the plants, depending on the properties of the safeners. Pre-emergence treatment includes the treatment of the area under cultivation prior to drilling as well as the treatment of the drilled areas under cultivation before the emergence of vegetation. Post-emergence application together with the herbicide is preferred. Tank mixes or finished formulations can be used for this purpose.

Compared with the seed-dressing method, the method in which herbicide and safener are used together post-emergence is a considerable practical advantage. Since application together only requires one operation, the farmer saves considerable expenses and, above all, a complicated seed-dressing step, which requires specific equipment, can be dispensed with. In contrast, the operational expense for the additional application of the safener can be virtually neglected, especially when herbicide and safener are used and applied as a finished formulation.

Depending on the indication and the herbicide used, the safener dosage rates required can vary within wide limits and are generally in the range from 0.001 to 5 kg, preferably 0.005 to 0.5 kg, of active substance per hectare.

The present invention therefore also relates to a method of protecting crop plants against phytotoxic secondary effects of herbicides of the A) type mentioned, which comprises treating the plants, seeds of the plants or areas under cultivation post-emergence with an effective amount of a compound of the formulae (B1) or (B2) mentioned, before, after, or simultaneously with, the herbicide of the A) type mentioned, preferably together with the A) type herbicide, with the exception of an application of imidazolinone herbicides with compounds of the formula (B2) mentioned. The present invention also relates to a method of protecting corn plants against phytotoxic secondary effects of imidazolinone herbicides A), which comprises applying an effective amount of a compound of the formula (B2) mentioned together with the herbicide of the A) type mentioned post-emergence to the plants or the area under cultivation.

The compounds of the B) type and their combinations with one or more of the herbicides mentioned can be formulated in a variety of ways, depending on the prevailing biological and/or chemico-physical parameters. The following possibilities are, for example, suitable for formulation: wettable powders (WP), emulsifiable concentrates (EC), water-soluble powders (SP), water-soluble concentrates (SL), concentrated emulsions (EW) such as oil-in-water and water-in-oil emulsions, sprayable solutions or emulsions, capsule suspensions (CS), dispersions on an oil or water base (SC), suspoemulsions, suspension concentrates, dusts (DP), oil-mixable solutions (OL), dressing agents, granules (SR) in the form of micro-granules, spray granules, coated granules and adsorption granules, granules for soil application or application by broadcasting, water-soluble granules (SG), water-dispersible granules (WG), ULV formulations, microcapsules and waxes.

These abovementioned formulation types are known in principle and are described, for example, in: Winnacker-Küchler, "Chemische Technologie [Chemical Technology]", Volume 7, C. Hauser Verlag Munich, 4th Ed., 1986; Wade van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; Marsden "Solvents Guide", 2nd Ed., Interscience, N.Y. 1963; McCutcheon's, "Detergents and Emulsifiers Annual", MC Publ. Corp. Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, fertilizers and/or growth regulators may also be prepared on the basis of these formulations, for example in the form of a ready mix or as a tank mix.

Wettable powders are preparations which are uniformly dispersible in water and which, besides the active substance, also contain wetting agents, for example polyoxethylated alkylphenols, polyoxethylated fatty alcohols and fatty amines, fatty alcohol polyglycol ether sulfates, alkanesulfonates or alkyarylsulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active substance in an organic solvent, for example butanol, cyclohexanone, dimethylformamide, xylene and also higher-boiling aromatic compounds or hydrocarbons, with the addition of one or more emulsifiers. Examples of emulsifiers which can be used are: calcium salts of an alkylarylsulfonic acid, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products (for example block copolymers), alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc or natural clays, such as kaolin, bentonite and pyrophyllite, or diatomaceous earth.

Granules can be produced either by spraying the active substance onto absorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, the agrochemical preparations contain 0.1 to 99 percent by weight, in particular 0.1 to 95% by weight, of B) type active substances, or of the antidode/herbicide active substance mixture A) and B), and 1 to 99.9% by weight, in particular 5 to 99.8% by weight, of a solid or liquid additive and 0 to 25% by weight, in particular 0.1 to 25% by weight, of a surfactant.

The concentration of active substance in wettable powders is, for example, about 10 to 90% by weight,; the remainder to 100% by weight is composed of conventional formulation components. In the case of emulsifiable concentrates, the concentration of active substance is about 1 to 80% by weight. Formulations in the form of dusts usually contain about 1 to 20% by weight of active substances, sprayable solutions about 0.2 to 20% by weight of active substances. In the case of granules such as water-dispersible granules, the active substance content depends partly on whether the active compound is liquid or solid. As a rule, the content of the water-dispersible granules is between 10 and 90% by weight. In addition, the active substance formulations mentioned contain, if appropriate, the adhesives, wetting agents, dispersing agents, emulsifiers, penetrants, solvents, fillers or carriers which are conventional in each case.

For use, the formulations present in commercially available form, are diluted, if appropriate, in a customary manner, for example using water in the case of wettable powders, emulsifiable concentrates, dispersions and water-dispersible granules. Preparations in the form of dusts, granules and also sprayable solutions are usually not further diluted with other inert substances before use. Particularly good actvities of the compositions according to the invention can be achieved when, in addition" to the surfactants contained in the formulations, further wetting agents are added in concentrations from 0.1 to 0.5% by weight by the tank-mix method, for example non-ionic wetting agents or wetting agents of the fatty alcohol polyol ether sulfate type (see, for example, German Patent Application P 4029304.1). The "safener" dosage rate required varies with the external conditions such as, inter alia, temperature, humidity, and the nature of the herbicide used.

The examples which follow serve to illustrate the invention:

A. FORMULATION EXAMPLES a) A dust is obtained by mixing 10 parts by weight of a B) type compound or of an active substance mixture of an A) type herbicide with a B) type safener and 90 parts by weight of talc as inert substance and comminuting the mixture in a hammer mill.

b) A wettable powder which is readily dispersible in water is obtained by mixing 25 parts by weight of a B) type compound or of an active substance mixture of an A) type herbicide with a B) type safener and 64 parts by weight of kaolin-containing quartz as inert substance, 10 parts by weight of potassium ligninsulfonate and 1 part by weight of sodium oleoylmethyltaurinate as wetting and dispersing agent, and grinding the mixture in a pinned disk mill.

c) A dispersion concentrate which is readily dispersible in water is obtained by mixing 20 parts by weight of a B) type compound or of an active substance mixture of an A) type herbicide with a B) type safener with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of a B) type compound or of an active substance mixture of an A) type herbicide with a B) type safener with 75 parts by weight of cyclohexanone as the solvent and 10 parts by weight of oxethylated nonylphenol as the emulsifier.

e) Water-dispersible granules are obtained by mixing 75 parts by weight of a compound of the B) type or of an active substance mixture of an A) type herbicide and a B) type safener,
10 parts by weight of calcium ligninsulfonate.
5 parts by weight of sodium lauryl sulfate,
3 parts by weight of polyvinyl alcohol and
7 parts by weight of kaolin, grinding the mixture on a pinned disk mill, and granulating the powder in a fluidized bed by spraying on water as granulation liquid.

f) Water-dispersible granules are also obtained by homogenizing and precomminuting, on a colloid mill, 25 parts by weight of a B) type compound or of an active substance mixture of an A) type herbicide with a B) type safener,
5 parts by weight of sodium 2,2' -dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water, subsequently grinding the mixture on a bead mill, and spraying and drying the resulting suspension in a spray tower by means of a single-substance nozzle.

B. BIOLOGICAL EXAMPLES

The crop plants, broad-leaved weeds and grass weeds were grown in plastic pots in the open or in the greenhouse until they had reached the 4–5-leaf stage and then treated according to the invention post-emergence with compounds of the A) and B) types. The compounds of the A) and B) types were applied in the form of aqeuous suspensions or emulsions at a rate of 300 l of water/ha (converted). 4 weeks after the treatment, the plants were scored visually for any type of damage by the herbicides applied, and the extent of the sustained growth inhibition was particularly taken into account. The assessment was in percentages in comparison with untreated controls.

The results of the following tables demonstrate that the B) type compounds used according to the invention are capable of reducing severe herbicide damage on crop plants effectively. Even when massive overdoses of the herbicides are applied, severe damage which occurs in the crop plants is markedly reduced and minor damage is compensated for completely. Mixtures of herbicides and B) type compounds are therefore outstandingly suitable for selectively controlling weeds in crops such as cereals and corn.

EXAMPLE 1

| Herbicide | Safener | Dosage rate [g of A.I./ha] | % damage on crop plants and weeds | | | |
|---|---|---|---|---|---|---|
| | | | Wheat | Barley | MAIN | STME |
| Chlorimuron-ethyl | — | 100 | 70 | 60 | — | — |
| | | 50 | 65 | 55 | 99 | 99 |
| | | 25 | 55 | 50 | 99 | 93 |
| | | 12 | 45 | 45 | 98 | 93 |
| | | 6 | — | — | 97 | 80 |
| Chlorimuron-ethyl | + B2-1 | 100 + 100 | | 25 | — | — |
| | | 50 + 50 | 0 | 25 | — | — |
| | | 25 + 25 | 0 | 5 | 99 | 93 |
| | | 12 + 12 | 0 | 0 | 97 | 90 |
| | | 6 + 6 | — | — | 97 | 90 |
| Chlorimuron-ethyl | + B1-5 | 100 + 100 | 0 | 10 | — | — |
| | | 50 + 50 | 0 | 0 | 99 | 95 |
| | | 25 + 25 | 0 | 0 | 99 | 92 |
| | | 12 + 12 | 0 | 0 | 97 | 88 |
| | | 6 + 6 | — | — | 93 | 90 |
| Chlorimuron-ethyl | + B1-2 | 100 + 100 | 10 | 30 | — | — |
| | | 50 + 50 | 0 | 10 | 99 | 97 |
| | | 25 + 25 | 0 | 0 | 99 | 92 |
| | | 12 + 12 | 0 | 0 | 99 | 90 |
| | | 6 + 6 | — | — | 98 | 80 |

Abbreviations:
A.I. = Active ingredient (based on pure active substance)
MAIN = *Matricaria inodora* (camomile)
STME = *Stellaria media* (chickweed)
— = not tested
Experimental set-up: Pot trial in the open

EXAMPLE 2

| Herbicide | Safener | Dosage rate [g of A.I./ha] | % damage on crop plants and weeds | | | |
|---|---|---|---|---|---|---|
| | | | Wheat | Barley | ALMY | ECCR |
| Chlorimuron-ethyl | — | 25 | 85 | 80 | 99 | 100 |
| | | 12 | 75 | 70 | 99 | 99 |
| | | 6 | 55 | 50 | 90 | 99 |
| | | 3 | 40 | 45 | 70 | 94 |
| Chlorimuron-ethyl | + B1-1 | 25 + 25 | 0 | 0 | 97 | 99 |
| | | 12 + 12 | 0 | 0 | 95 | 99 |
| | | 6 + 6 | 0 | 0 | 95 | 98 |
| | | 3 + 3 | 0 | 0 | 90 | 80 |

Abbreviations:
A.I. = Active ingredient (based on pure active substance)
ALMY = *Allopecurus myosuroides*
ECCR = *Echinochloa crus-galli*
— = not tested
Experimental set-up:
Greenhouse trial; growth stage: wheat: 3–4 leaves, barley: 3–4 leaves, ALMY: 21; ECCR: 21, i.e. onset of tillering.

EXAMPLE 3

| Herbicide | Safener | Dosage rate [g of A.I./ha] | % damage on crop plants and weeds | | |
|---|---|---|---|---|---|
| | | | Wheat | Barley | *Digitaria sanguinalis* (large crab-grass) |
| Imazethapyr | — | 400 | 100 | 100 | 95 |
| | | 200 | 100 | 95 | 95 |
| | | 100 | 100 | 95 | 95 |
| | | 50 | 100 | 90 | 90 |
| Imazethapyr | + B1-1 | 400 + 200 | 80 | 10 | 95 |
| | | 200 + 100 | 55 | 0 | 95 |
| | | 100 + 50 | 10 | 0 | 95 |
| | | 50 + 25 | 0 | 0 | 90 |
| Imazethapyr | + B1-4 | 400 + 200 | — | 90 | 95 |

-continued

| Herbicide | Safener | Dosage rate [g of A.I./ha] | % damage on crop plants and weeds | | |
|---|---|---|---|---|---|
| | | | Wheat | Barley | *Digitaria sanguinalis* (large crab-grass) |
| | | 200 + 100 | — | 15 | 95 |
| | | 100 + 50 | — | 10 | 93 |
| | | 50 + 25 | — | 0 | 90 |
| Imazethapyr | + B2-1 | 400 + 200 | 97 | 20 | 99 |
| | | 200 + 100 | 20 | 10 | 99 |
| | | 100 + 50 | 10 | 0 | 98 |
| | | 50 + 25 | 0 | 0 | 95 |
| Imazaquin | — | 400 | 100 | 100 | 99 |
| | | 200 | 100 | 100 | 95 |
| | | 100 | 100 | 100 | 90 |
| | | 50 | 100 | 100 | 75 |
| Imazaquin | + B2-1 | 400 + 200 | 95 | — | 95 |
| | | 200 + 100 | 60 | — | 95 |
| | | 100 + 50 | 10 | — | 93 |
| | | 50 + 25 | 0 | — | 90 |

Abbreviations:
A.I. = Active ingredient (based on pure active substance)
— = not tested
Experimental set-up: Greenhouse trial

EXAMPLE 4

| Herbicide | Safener | Dosage rate [g of A.I./ha] | % damage on crop plants and weeds | | |
|---|---|---|---|---|---|
| | | | Corn | AMRE | SEFA |
| Amidosulfuron | — | 100 | 90 | 100 | — |
| | | 50 | 50 | 100 | — |
| | | 25 | 30 | 100 | — |
| | | 12 | 20 | 98 | — |
| Amidosulfuron | + B2-2 | 100 + 100 | 5 | 100 | — |
| | | 50 + 50 | 0 | 100 | — |
| | | 25 + 25 | 0 | 99 | — |
| | | 12 + 12 | 0 | 98 | — |
| SH1 | — | 100 | 90 | — | 100 |
| | | 50 | 90 | — | 100 |
| | | 25 | 70 | — | 99 |
| | | 12 | 35 | — | 98 |
| SH1 | + B2-2 | 100 + 100 | 10 | — | 100 |
| | | 50 + 50 | 0 | — | 100 |
| | | 25 + 25 | 0 | — | 99 |
| | | 12 + 12 | 0 | — | 97 |
| SH2 | — | 100 | 70 | — | 100 |
| | | 50 | 55 | — | 100 |
| | | 25 | 20 | — | 100 |
| | | 12 | 0 | — | 99 |
| SH2 | + B2-2 | 100 + 100 | 0 | — | 100 |
| | | 50 + 50 | 0 | — | 100 |
| | | 25 + 25 | 0 | — | 100 |
| | | 12 + 12 | 0 | — | 98 |

Abbreviations:
A.I. = Active ingredient (based on pure active substance)
— = not tested
SH1 = 3-(4,6-Dimethoxypyrimidin-2-yl)-1-[3-(N-methyl-N-methylsulfonyl-amino)-2-pyridyl-sulfonyl]urea (example of a herbicide from Group 5c)
SH2 = DPX-E 9636 (sulfonylurea, Herbicide 5b)
AMRE = *Amarantus retroflexus* (dicotyledon)
SEFA = *Setaria faberii* (millet, monocotyledon)
Experimental set-up: Pot trial in the open

EXAMPLE 5

| Herbicide | Safener | Dosage rate [g of A.I./ha] | % damage on crop plants and weeds | | |
|---|---|---|---|---|---|
| | | | Corn | AMRE | SEFA |
| SH1 | — | 100 | 90 | 100 | 100 |
| | | 50 | 50 | 100 | 100 |
| | | 25 | 30 | 100 | 99 |
| | | 12 | 20 | 98 | 98 |
| SH1 | + B2-3 | 100 + 100 | 5 | 100 | 100 |
| | | 50 + 50 | 0 | 100 | 100 |
| | | 25 + 35 | 0 | 98 | 99 |
| SH1 | + B2-4 | 100 | 5 | 100 | 100 |
| | | 50 | 0 | 100 | 100 |
| | | 25 | 0 | 95 | 100 |
| SH1 | + B2-5 | 100 + 100 | 10 | 100 | 100 |
| | | 50 + 50 | 5 | 99 | 100 |
| | | 25 + 25 | 0 | 95 | 95 |
| SH1 | + B1-8 | 100 + 100 | 15 | 100 | 100 |
| | | 50 + 50 | 5 | 100 | 100 |
| | | 25 + 25 | 0 | 98 | 98 |
| SH1 | + B2-6 | 100 + 100 | 10 | 100 | 100 |
| | | 50 + 50 | 0 | 100 | 100 |
| SH1 | + B2-7 | 100 + 100 | 5 | 100 | 100 |
| | | 50 + 50 | 0 | 100 | 100 |
| SH1 | + B2-9 | 100 + 100 | 10 | 100 | 100 |
| | | 50 + 50 | 0 | 100 | 99 |
| SH1 | + B2-11 | 100 + 100 | 10 | 100 | 100 |
| | | 50 + 50 | 0 | 100 | 100 |

Abbreviations: See Table in Example 4

EXAMPLE 6

| Herbicide | Safener | Dosage rate [g of A.I./ha] | % damage on corn |
|---|---|---|---|
| SH1 | — | 50 | 90 |
| | | 25 | 75 |
| | | 12 | 35 |
| SH1 | + B2-12 | 50 + 50 | 5 |
| | | 25 + 25 | 0 |
| | | 12 + 12 | 0 |
| SH1 | + B2-13 | 50 + 50 | 0 |
| | | 25 + 25 | 0 |
| | | 12 + 12 | 0 |
| SH1 | + B2-14 | 50 + 50 | 10 |
| | | 25 + 25 | 0 |
| | | 12 + 12 | 0 |
| SH1 | + B2-15 | 50 + 50 | 20 |
| | | 25 + 25 | 10 |
| | | 12 + 12 | 0 |
| SH1 | + B2-16 | 50 + 50 | 5 |
| | | 25 + 25 | 0 |
| SH1 | + B2-17 | 50 + 50 | 10 |
| | | 25 + 25 | 0 |
| SH1 | + B2-18 | 50 + 50 | 5 |
| | | 25 + 25 | 0 |
| SH1 | + B2-19 | 50 + 50 | 5 |
| | | 25 + 25 | 0 |
| SH1 | + B2-20 | 50 + 50 | 5 |
| | | 25 + 25 | 0 |
| SH1 | + B2-21 | 50 + 50 | 10 |
| | | 25 + 25 | 10 |
| SH1 | + B2-22 | 50 + 50 | 10 |
| | | 25 + 25 | 0 |
| SH1 | + B2-23 | 50 + 50 | 25 |
| | | 25 + 25 | 5 |
| SH1 | + B2-24 | 50 + 50 | 30 |
| | | 25 + 25 | 5 |
| SH1 | + B2-23 | 50 + 50 | 15 |
| | | 25 + 25 | 0 |

Abbreviations:
A.I. = Active ingredient (based on pure active substance)
— = not tested

| Herbicide | Safener | Dosage rate [g of A.I./ha] | % damage on corn |
|---|---|---|---|

SH1 = 3-(4,6-Dimethoxypyrimidin-2-yl)-1-[3-(N-methyl-N-methylsulfonyl-amino)-2-pyridyl-sulfonyl]urea (Example of a herbicide from Group 5c)
Experimental set-up: Pot trial in the open

EXAMPLE 7 (Pot trial in the open)

| Herbicide | Safener | Dosage rate [g of A.I./ha] | % damage on crop plants and weeds | |
|---|---|---|---|---|
| | | | Corn | SEFA |
| SH2 | + B2-3 | 50 | 55 | 100 |
| | | 25 | 20 | 100 |
| | | 12 | 0 | 99 |
| SH2 | + B2-3 | 50 + 50 | 0 | 100 |
| | | 25 + 25 | 0 | 100 |
| | | 12 + 12 | 0 | 98 |
| SH2 | + B2-4 | 50 + 50 | 0 | 100 |
| | | 25 + 25 | 0 | 100 |
| | | 12 + 12 | 0 | 95 |
| SH2 | + B2-5 | 50 + 50 | 0 | 100 |
| | | 25 + 35 | 0 | 100 |
| | | 12 + 12 | 0 | 99 |
| SH2 | + B2-6 | 50 + 50 | 0 | 100 |
| | | 25 + 25 | 0 | 100 |
| | | 12 + 12 | 0 | 98 |
| SH2 | + B2-7 | 50 + 50 | 0 | 100 |
| | | 25 + 25 | 0 | 100 |
| SH2 | + B2-8 | 50 + 50 | 0 | 100 |
| | | 25 + 25 | 0 | 100 |
| SH2 | + B2-10 | 50 + 50 | 0 | 100 |
| | | 25 + 25 | 0 | 100 |
| SH2 | + B1-8 | 50 + 50 | 0 | 100 |
| | | 25 + 25 | 0 | 100 |

Abbreviations:
A.I. = Active ingredient (based on pure active substance)
SH2 = DPX-E 9636 (sulfonylurea, Herbicide 5b)
SEFA = *Setaria faberii* (millet, monocotyledon)

EXAMPLE 8 (Pot trial in the open)

| Herbicide | Safener | Dosage rate [g of A.I./ha] | % damage on crop plants and weeds | |
|---|---|---|---|---|
| | | | Corn | SEFA |
| Primisulfuron | | 100 | 50 | 100 |
| | | 50 | 25 | 98 |
| | | 25 | 10 | 90 |
| Primisulfuron | + B1-8 | 100 + 50 | 0 | 100 |
| | | 50 + 25 | 0 | 100 |
| | | 25 + 12 | 0 | 90 |
| Primisulfuron | + B2-2 | 100 + 50 | 0 | 100 |
| | | 50 + 25 | 0 | 95 |
| | | 25 + 12 | 0 | 95 |
| Primisulfuron | + B2-3 | 100 + 50 | 0 | 100 |
| | | 50 + 25 | 0 | 98 |
| | | 25 + 12 | 0 | 95 |
| Primisulfuron | + B2-4 | 100 + 50 | 0 | 100 |
| | | 50 + 25 | 0 | 98 |
| | | 25 + 12 | 0 | 90 |
| Primisulfuron | + B2-5 | 100 + 100 | 0 | 100 |
| | | 50 + 50 | 0 | 100 |
| Primisulfuron | + B2-6 | 100 + 100 | 0 | 100 |
| | | 50 + 50 | 0 | 95 |
| Primisulfuron | + B2-7 | 100 + 100 | 0 | 100 |
| | | 50 + 50 | 0 | 95 |
| Primisulfuron | + B2-8 | 100 + 100 | 0 | 100 |
| | | 50 + 50 | 0 | 90 |
| Primisulfuron | + B2-9 | 100 + 100 | 0 | 100 |

| Herbicide | Safener | Dosage rate [g of A.I./ha] | % damage on crop plants and weeds | |
|---|---|---|---|---|
| | | | Corn | SEFA |
| | | 50 + 50 | 0 | 95 |

Abbreviations:
See Table 4

EXAMPLE 9

| Herbicide | Safener | Dosage rate [g of A.I./ha] | % damage on crop plants and weeds | | |
|---|---|---|---|---|---|
| | | | Corn | AMRE | SEFA |
| Imazethapyr | — | 200 | 60 | 90 | 100 |
| | | 100 | 30 | 90 | 98 |
| | | 50 | 20 | 75 | 95 |
| Imazethapyr | + B1-8 | 200 + 100 | 10 | 95 | 100 |
| | | 100 + 50 | 0 | 90 | 99 |
| | | 50 + 25 | 0 | 80 | 90 |
| Imazethapyr | + B2-3 | 200 + 100 | 5 | 95 | 100 |
| | | 100 + 50 | 0 | 95 | 98 |
| | | 50 + 25 | 0 | 80 | 95 |
| Imazethapyr | + B2-4 | 200 + 100 | 10 | 95 | 100 |
| | | 100 + 50 | 0 | 90 | 99 |
| | | 50 + 25 | 0 | 75 | 90 |
| Imazethapyr | + B2-5 | 200 + 100 | 15 | 95 | 100 |
| | | 100 + 50 | 0 | 90 | 99 |
| | | 50 + 25 | 0 | 80 | 95 |
| Imazethapyr | + B2-6 | 200 + 100 | 20 | 95 | 100 |
| | | 100 + 50 | 0 | 95 | 98 |
| | | 50 + 25 | 0 | 85 | 90 |
| Imazethapyr | + B2-7 | 200 + 100 | 5 | 95 | 100 |
| | | 100 + 50 | 0 | 90 | 95 |
| | | 50 + 25 | 0 | 80 | 90 |
| Imazethapyr | + B2-10 | 200 + 100 | 15 | 98 | 100 |
| | | 100 + 50 | 0 | 90 | 98 |

Abbreviations:
See Table in Example 4

EXAMPLE 10

| Herbicide | Safener | Dosage rate [g of A.I.ha] | % damage on corn (cv. Felix) |
|---|---|---|---|
| Thifenuron-methyl | — | 60 | 50 |
| | | 30 | 25 |
| | | 15 | 10 |
| Thifenuron-methyl | + B2-3 | 60 + 60 | 20 |
| | | 30 + 30 | 0 |
| | | 15 + 30 | 0 |
| Thifenuron-methyl | + B2-4 | 60 + 60 | 10 |
| | | 30 + 30 | 0 |
| | | 15 + 15 | 0 |
| Thifenuron-methyl | + B2-5 | 60 + 60 | 10 |
| | | 30 + 30 | 0 |
| | | 15 + 15 | 0 |
| Thifenuron-methyl | + B2-6 | 60 + 60 | 5 |
| | | 30 + 30 | 0 |
| | | 15 + 15 | 0 |
| Thifenuron-methyl | + B2-7 | 60 + 60 | 10 |
| | | 30 + 30 | 0 |
| | | 15 + 15 | 0 |
| Thifenuron-methyl | + B2-8 | 60 + 60 | 5 |
| | | 30 + 30 | 0 |
| | | 15 + 15 | 0 |
| Thifenuron-methyl | + B2-11 | 60 + 60 | 10 |
| | | 30 + 30 | 0 |
| | | 15 + 15 | 0 |

EXAMPLE 11

| Herbicide | Safener | Dosage rate [g of A.I.ha] | % damage on corn (cv. Felix) |
|---|---|---|---|
| Nicosulfuron | — | 400 | 40 |
|  |  | 200 | 30 |
|  |  | 100 | 20 |
| Nicosulfuron | + B1-8 | 400 + 200 | 0 |
|  |  | 200 + 100 | 0 |
|  |  | 100 + 50 | 0 |
| Nicosulfuron | + B2-3 | 400 + 200 | 0 |
|  |  | 200 + 100 | 0 |
|  |  | 100 + 50 | 0 |
| Nicosulfuron | + B2-4 | 400 + 200 | 0 |
|  |  | 200 + 100 | 0 |
|  |  | 100 + 50 | 0 |
| Nicosulfuron | + B2-5 | 400 + 200 | 0 |
|  |  | 200 + 100 | 0 |
|  |  | 100 + 50 | 0 |
| Nicosulfuron | + B2-6 | 400 + 200 | 0 |
|  |  | 200 + 100 | 0 |
|  |  | 100 + 50 | 0 |
| Nicosulfuron | + B2-8 | 400 + 200 | 0 |
|  |  | 200 + 100 | 0 |
|  |  | 100 + 50 | 0 |
| Nicosulfuron | + B2-10 | 400 + 200 | 0 |
|  |  | 200 + 100 | 0 |

Abbreviations:
See Table in Example 4

EXAMPLE 12

| Herbicide | Safener | Dosage rate [g of A.I.ha] | % damage on corn (cv. Felix) |
|---|---|---|---|
| SH3 | — | 400 | 50 |
|  |  | 200 | 30 |
|  |  | 100 | 10 |
| SH3 | + B2-5 | 400 + 200 | 5 |
|  |  | 200 + 100 | 0 |
|  |  | 100 + 50 | 0 |
| SH3 | + B2-6 | 400 + 200 | 0 |
|  |  | 200 + 100 | 0 |
|  |  | 100 + 50 | 0 |
| SH3 | + B2-3 | 400 + 200 | 10 |
|  |  | 200 + 100 | 0 |
|  |  | 100 + 50 | 0 |
| SH3 | + B1-8 | 400 + 200 | 10 |
|  |  | 200 + 100 | 0 |
|  |  | 100 + 50 | 0 |
| SH3 | + B2-8 | 400 + 200 | 5 |
|  |  | 200 + 100 | 0 |
|  |  | 100 + 50 | 0 |
| SH3 | + B2-10 | 400 + 200 | 10 |
|  |  | 200 + 100 | 0 |

Abbreviations:
A.I. = Active ingredient (based on pure active substance)
SH3 = 3-(4,6-Dimethoxypyrimidin-2-yl)-1-[6-methyl-3-(N-methyl-N-methylsulfonyl-amino)-2-pyridylk-sulfonyl]-urea (Example of a herbicide from Group 5c)
Experimental set-up: Pot trial in the open

We claim:
1. A herbicidal composition which comprises an effective amount of
   A) one or more herbicides from the group of the sulfonylureas and
   B) one or more compounds of the formula B2,

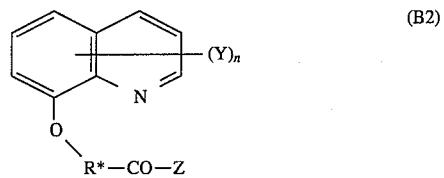

in which
Y is 5-Cl
$R^*$ is a $C_1$–$C_2$-alkylene chain which can additionally be substituted by one or two $C_1$–$C_4$-alkyl radicals, and
Z is $OR^1$,
$R^1$ independently of R is hydrogen, $C_1$–$C_{18}$-alkyl, $C_3$–$C_{12}$-cycloalkyl, $C_2$–$C_8$-alkenyl or $C_2$–$C_8$-alkynyl, each of the above carbon-containing radicals independently of one another being unsubstituted or monosubstituted or polysubstituted by radicals selected from the group consisting of halogen, hydoxyl, $C_1$–$C_8$-alkoxy, $C_1$–$C_8$-alkylthio, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy, cyano, mono- and di-($C_1$–$C_4$-alkyl)amino, ($C_1$–$C_8$-alkoxy)carbonyl, ($C_2$–$C_8$-alkenyl-oxy)carbonyl, ($C_1$–$C_8$-alkylthio)carbonyl, ($C_2$–$C_8$-alkynyloxy)carbonyl, ($C_1$–$C_8$-alkyl)carbonyl, ($C_2$–$C_8$-alkenyl)carbonyl, ($C_2$–$C_8$-alkynyl)carbonyl, 1-(hydroxyimino)-$C_1$–$C_6$-alkyl, 1-($C_1$–$C_4$-alkylimino)-$C_1$–$C_6$-alkyl, 1-($C_1$–$C_4$-alkoxyimino)-$C_1$–$C_6$-alkyl, ($C_1$–$C_8$alkyl)carbonylamino, ($C_2$–$C_8$-alkenyl)carbonyl-amino, ($C_2$–$C_8$-alkynyl)carbonylamino, aminocarbonyl, ($C_1$–$C_8$-alkyl)aminocarbonyl, di-($C_1$–$C_6$-alkyl)aminocarbonyl, ($C_2$–$C_6$-alkenyl)aminocarbonyl, ($C_2$–$C_6$-alkynyl)aminocarbonyl, ($C_1$–$C_8$-alkoxy)carbonylamino, ($C_1$–$C_8$-alkyl)aminocarbonylamino, $C_1$–$C_6$-alkylcarbonyloxy which is unsubstituted or substituted by halogen, $NO_2$, $C_1$–$C_4$-alkoxy or optionally substituted phenyl, ($C_2$–$C_6$-alkenyl)carbonyloxy, ($C_2$–$C_6$-alkynyl)carbonyloxy, $C_1$–$C_8$-alkylsulfonyl, phenyl, phenyl-$C_1$–$C_6$-alkoxy, phenyl-($C_1$–$C_6$-alkoxy)carbonyl, phenoxy, phenoxy-$C_1$–$C_6$-alkoxy, phenoxy-($C_1$–$C_6$-alkoxy)carbonyl, phenylcarbonyloxy, phenylcarbonylamino, phenyl-($C_1$–$C_6$-alkyl)carbonylamino, where the 9 last-mentioned radicals in the phenyl ring are unsubstituted or monosubstituted or polysubstituted by radicals selected from the group consisting of halogen, $C_1$–$C_4$-alkyl, $C_1$–$C_4$-alkoxy, $C_1$–$C_4$-haloalkyl, $C_1$–$C_4$-haloalkoxy and nitro, and radicals of the formulae —$SiR'_3$, —$OSiR'_3$, $(R')_3Si$-$C_1$–$C_6$-alkoxy, —CO—O—$NR'_2$, —O—N=$CR'_2$, —N=$CR'_2$, —O—$NR'_2$—CH($OR'$)$_2$ and —O—($CH_2$)$_m$—CH($OR'$)$_2$, where the R' radicals in the formulae mentioned independently of each other are hydrogen, $C_1$–$C_4$-alkyl or phenyl which is unsubstituted or monosubstituted or polysubstituted by radicals selected from the group consisting of halogen, $C_1$–$C_4$-alkyl, $C_1$–$C_4$-alkoxy, $C_1$–$C_4$-haloalkyl, $C_1$–$C_4$-haloalkoxy and nitro, or, in pairs, are a $C_2$–$C_6$-alkylene chain and m=0 to 6, and an alkoxy radical of the formula R"O—CHR'''(OR")-$C_1$–$C_6$-alkoxy where the R" radicals independently of each other are $C_1$–$C_4$-alkyl or together are a $C_1$–$C_6$- alkylene group, and R''' is hydrogen or $C_1$–$C_4$-alkyl, and n is 1.

2. A composition as claimed in claim 1, wherein $R^1$ is hydrogen, $C_1$–$C_{12}$-alkyl, $C_3$–$C_7$-cycloalkyl, $C_2$–$C_8$-alkenyl or $C_2$–$C_8$-alkynyl, where each of the above carbon-containing radicals independently of each other is unsubstituted or monosubstituted or polysubstituted by halogen or monosubstituted or disubstituted by radicals selected from the group consisting of hydroxyl, $C_1$–$C_4$-alkoxy, $C_1$–$C_4$-alkythio, $C_2$–$C_4$-alkenyloxy, $C_2$–$C_4$-alkynyloxy, mono- and di-($C_1$–$C_2$-alkyl)-amino, ($C_1$–$C_4$-alkoxy)carbonyl, ($C_2$–$C_4$-alkenyloxy)carbonyl, ($C_2$–$C_4$-alkynyloxy)carbonyl, ($C_1$–$C_4$-alkyl)carbonyl, ($C_2$–$C_4$-alkenyl)carbonyl, ($C_2$–$C_4$-alkynyl)carbonyl, 1-(hydroxyimino)-$C_1$–$C_4$-alkyl, 1-($C_1$–$C_4$-alkylimino)-$C_1$–$C_4$-alkyl, 1-($C_1$–$C_4$-alkoxyimino)-$C_1$–$C_4$-alkyl, $C_1$–$C_4$-alkylsulfonyl, phenyl, phenyl-$C_1$–$C_4$-alkoxy, phenyl-($C_1$–$C_4$alkoxy)carbonyl, phenoxy, phenoxy-$C_1$–$C_4$-alkoxy, phenoxy-($C_1$–$C_4$-alkoxy)carbonyl, where the 6 last-mentioned radicals are unsubstituted or monosubstituted or polysubstituted in the phenyl ring by radicals selected from the group consisting of halogen, $C_1$–$C_2$-alkyl, $C_1$–$C_2$-alkoxy, $C_1$–$C_2$-haloalkyl, $C_1$–$C_2$-haloalkoxy and nitro, and radicals of the formulae —SiR'$_3$, —O—N=CR'$_2$, —N=CR', and —O—NR'$_2$, where the R' radicals in the formulae mentioned independently of each other are hydrogen, $C_1$–$C_2$-alkyl or phenyl which is unsubstituted or monosubstituted or polysubstituted by radicals selected from the group consisting of halogen, $C_1$–$C_2$-haloalkoxy and nitro, or, in pairs, are a $C_4$–$C_5$-alkylene chain.

3. A composition as claimed in claim 1, wherein, in the compounds of the formula B2, Y is 5-Cl, Z is a radical of the formula $OR^1$, R* is $CH_2$ and $R^1$ is hydrogen, $C_1$–$C_8$-alkyl, $C_1$–$C_8$-haloalkyl, ($C_1$–$C_4$-alkoxy)-$C_1$–$C_4$-alkyl, 1-(hydroxyimino)-$C_1$–$C_4$-alkyl, or 1-($C_1$–$C_4$-alkylamino)-$C_1$–$C_3$-alkyl.

4. A herbicidal composition which comprises an effective amount of A) 3-(4,6-dimethoxypyrimidin-2-yl)-1-[3-(N-methyl-N-methylsulfonyl-amino)-2 -pyridyl-sulfonyl]urea and B) B2) 2-allyloxy-1-methylethyl 2 -(5-chloro-8-quinolinoxy)acetate.

5. A composition as claimed in claim 1, which comprises one or more herbicides selected from the group consisting of phenylsulfonylureas, thienylsulfonylureas, pyrazolesulfonylureas, sulfonediamide derivatives, pyridylsulfonylureas, phenoxysulfonylureas.

6. A composition as claimed in claim 1, which comprises one or more herbicides selected from the group consisting of chlorimuron-ethyl, nicosulfuron, DPX-E 9636, amidosulfuron, thiameturon-methyl, primisulfuron, pyridylsulfonylureas of the formula A1 or their salts,

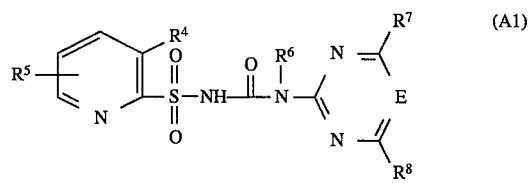

(A1)

which

E is CH or N, $R^4$ is iodine or $NR^9R^{10}$, $R^5$ is H, halogen, cyano, $C_1$–$C_3$-alkyl, $C_1$–$C_3$-alkoxy, $C_1$–$C_3$-haloalkyl, $C_1$–$C_3$-haloalkoxy, $C_1$–$C_3$-alkylthio, ($C_1$–$C_3$-alkoxy)-$C_1$–$C_3$-alkyl, ($C_1$–$C_3$-alkoxy)-carbonyl, mono- or di-($C_1$–$C_3$-alkyl)-amino, $C_1$–$C_3$-alkyl-sulfonyl or -sulfonyl, $SO_2$-$NR^aR^b$ or $CO$-$NR^aP^b$, $R^a$ and $R^b$ independently of each other are H, $C_1$–$C_3$-alkyl, $C_1$–$C_3$-alkenyl, $C_1$–$C_3$-alkynyl or together are —$(CH_2)_4$—, —$(CH_2)_5$— or —$(CH_2)_2$—O—$(CH_2)_2$—, $R^6$ is H or $CH_3$, $R^7$ is halogen, $C_1$–$C_2$-alkyl, $C_1$–$C_2$-alkoxy, $C_1$–$C_2$-haloalkyl, $C_1$–$C_2$-haloalkoxy or $OCH_2CF_3$, $R^8$ is $C_1$–$C_2$-alkyl, $C_1$–$C_2$-haloalkoxy or $C_1$–$C_2$-alkoxy and $R^9$ is $C_1$–$C_4$-alkyl and $R^{10}$ is $C_1$–$C_4$-alkylsulfonyl or $R^9$ and $R^{10}$ together are a chain of the formula —$(CH_2)SO_2$— or —$(CH_2)_4SO_2$—, alkoxyphenoxysulfonylureas of the formula A2 or their salts

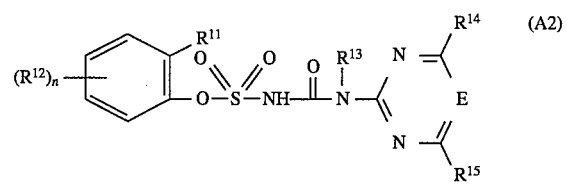

(A2)

in which

E is CH or N, $R^{11}$ is ethoxy, propoxy or isopropoxy, $R^{12}$ is hydrogen, halogen, $NO_2$, $CF_3$, CN, $C_1$–$C_4$-alkyl, $C_1$–$C_4$-alkoxy, $C_1$–$C_4$-alkylthio or ($C_1$–$C_3$-alkoxy)carbonyl, n is 1, 2 or 3, $R^{13}$ is halogen, $C_1$–$C_4$-alkyl or $C_3$–$C_4$-alkenyl, $R^{14}$ and $R^{15}$ independently of each other are halogen, $C_1$–$C_2$-alkyl, $C_1$–$C_2$-alkoxy, $C_1$–$C_2$-haloalkyl, $C_1$–$C_2$-haloalkoxy or ($C_1$–$C_2$-alkoxy)-$C_1$–$C_2$-alkyl, 3-(4-ethyl-6-methoxy-1,3,5-triazin-2-yl)-1-(2,3-dihydro-1,1-dioxo-2 -methylbenzo[b]thiophen-7-sulfonyl)urea, 3-(4-ethoxy-6-ethyl-1,3,5-triazin-2-yl)-1-(2,3-dihydro-1,1-dioxo-2 -methylbenzo[b]thiophen-7-sulfonyl)urea.

7. A composition as claimed in claim 1, wherein the ratio by weight of safener:herbicide is in a range from 1:10 to 10:1.

8. A composition as claimed in claim 1, which comprises 0.1 to 99 percent by weight of active substances of the B) type or of the antidote/herbicide active substance mixture A) and B), and 1 to 99.9% by weight of a solid or liquid additive and 0 to 25% by weight of a surfactant.

9. A method of protecting crop plants against phytotoxic secondary effects of herbicides of the A) type as defined in claim 1, which comprises applying an effective amount of a compound of the formula (B2), as is defined in claim 1, to the plants, seeds of the plants or the area under cultivation, before, after or simultaneously with, the herbicide of the type A).

10. A method as claimed in claim 9, wherein the crop plants are cereal plants or corn plants.

11. The method as claimed in claim 9, wherein the B) type safener is applied at an application rate of 0.001 to 5 kg of active ingredient/ha and a ratio by weight of safener:herbicide in a range from 1:10 to 10:1.

* * * * *